US011585770B2

United States Patent
Yu et al.

(10) Patent No.: US 11,585,770 B2
(45) Date of Patent: Feb. 21, 2023

(54) IN SITU DETERMINATION OF ALUM FILLING EVENNESS AND SEDIMENTATION IN PHARMACEUTICAL PRODUCTS USING WATER PROTON NMR

(71) Applicants: UNIVERSITY OF MARYLAND, BALTIMORE, Baltimore, MD (US); ACCESS TO ADVANCED HEALTH INSTITUTE, Seattle, WA (US)

(72) Inventors: Yihua (Bruce) Yu, Ellicott City, MD (US); Marc Taraban, North Potomac, MD (US); Christopher Fox, Sumner, WA (US)

(73) Assignees: UNIVERSITY OF MARYLAND, BALTIMORE, Baltimore, MD (US); ACCESS TO ADVANCED HEALTH INSTITUTE, Seattle, WA (US)

( * ) Notice: Subject to any disclaimer, the term of this patent is extended or adjusted under 35 U.S.C. 154(b) by 462 days.

(21) Appl. No.: 16/593,145

(22) Filed: Oct. 4, 2019

(65) Prior Publication Data

US 2020/0110046 A1    Apr. 9, 2020

Related U.S. Application Data

(60) Provisional application No. 62/741,142, filed on Oct. 4, 2018.

(51) Int. Cl.
*G01N 24/08* (2006.01)
*G01N 33/15* (2006.01)
(52) U.S. Cl.
CPC ........... *G01N 24/082* (2013.01); *G01N 33/15* (2013.01)

(58) Field of Classification Search
CPC .... G01N 24/082; G01N 33/15; G01N 24/085; G01R 33/448
See application file for complete search history.

(56) References Cited

U.S. PATENT DOCUMENTS

| | | | |
|---|---|---|---|
| 6,307,372 B1 * | 10/2001 | Sugarman | G01R 33/44 422/67 |
| 8,314,618 B2 | 11/2012 | Bieri et al. | |
| 8,854,038 B2 | 10/2014 | Hernando et al. | |
| 8,862,407 B2 | 10/2014 | Chugunov et al. | |
| 9,194,925 B2 | 11/2015 | Zhong et al. | |
| 10,267,754 B2 | 4/2019 | Yu et al. | |
| 10,514,347 B2 | 12/2019 | Yu et al. | |
| 2004/0090231 A1 | 5/2004 | Augustine et al. | |
| 2005/0287527 A1 | 12/2005 | Ni et al. | |
| 2006/0269965 A1 | 11/2006 | Josephson | |
| 2007/0116602 A1 | 5/2007 | Lee | |

(Continued)

OTHER PUBLICATIONS

Notice of Allowance for U.S. Appl. No. 16/369,534.

(Continued)

*Primary Examiner* — Jay Patidar
(74) *Attorney, Agent, or Firm* — Tristan A. Fuierer; Casimir Jones SC (57) ABSTRACT

A method of using the transverse relaxation rate ($R_2$) of solvent NMR signal to noninvasively assess alum-containing products such as vaccines. This technique can be used for quality control in vaccine manufacturing (e.g., fill-finish step) to determine the evenness of alum filling level as well as extent of alum particle sedimentation in filled and sealed products.

20 Claims, 2 Drawing Sheets

(56) References Cited

U.S. PATENT DOCUMENTS

| | | | |
|---|---|---|---|
| 2007/0152666 A1* | 7/2007 | Thesen | G01N 24/08 324/307 |
| 2010/0047180 A1 | 2/2010 | Zeng et al. | |
| 2010/0072994 A1 | 3/2010 | Lee et al. | |
| 2010/0278829 A1 | 11/2010 | Edwards, III et al. | |
| 2011/0124744 A1 | 5/2011 | Lee et al. | |
| 2012/0100546 A1 | 4/2012 | Lowery, Jr. et al. | |
| 2012/0164644 A1* | 6/2012 | Neely | C12Q 1/6816 435/6.11 |
| 2013/0244238 A1 | 9/2013 | Neely et al. | |
| 2013/0265054 A1 | 10/2013 | Lowery, Jr. | |
| 2016/0047761 A1 | 2/2016 | Yu et al. | |
| 2017/0176359 A1* | 6/2017 | Graessl | G01N 24/08 |
| 2018/0052122 A1* | 2/2018 | Davis | G01R 33/445 |
| 2018/0113141 A1* | 4/2018 | Lowery, Jr. | A61B 5/0263 |
| 2019/0293579 A1 | 9/2019 | Yu et al. | |
| 2019/0391218 A1 | 12/2019 | Yu et al. | |

OTHER PUBLICATIONS

International Search Report and Written Opinion, dated Feb. 20, 2018.
Yu, Bruce, et al.; Water Proton NMR for Noninvasive Chemical Analysis and Drug Product Inspection,: American Pharmaceutical Review, 2017, 20, 34-39.
Taraban, Marc B., et al.; "Water Proton NMR: A Tool for Protein Aggregation Characterization," Anal. Chem., 2017, pp. 5494-5502, vol. 89; DOI: 10.1021/acs.analchem.7b00464.
Bouchoux, Antoine et al. "Molecular Mobility in Dense Protein Systems: An Investigation through 1 H NFM Relaxometry and Diffusometry," Journal of Physical Chemistry Part B: Condensed Matter, Materials, Surfaces, Interfaces & Biophysical, 2012 (116) (38), 11744-11753.
Daskiewicz, O. et al. "Proton Magnetic Relaxation and Protein Hydration." Nature, 1963 (200) (4910), 1006-1007.
Mahler, Hans-Christian et al. "Protein aggregation: Pathways, induction factors and analysis." Journal of Pharmaceutical Sciences, 2009 (98)(9), 2909-2925.
Baroni, et al.; "Relaxometric Characterization of Balsamic Vinegar," meeting abstract 6th Conference on Field Cycling NMR Relaxometry Turin (Italy) Jun. 4, 2009.
Bloembergen, N. et al.; "Relaxation Effects in Nuclear Magnetic Resonance absorption," Phys. Rev. 1948, 73, 679-712.
Dalvit, C. et al.; "High-Throughput NMR-Based Screening with Competition Binding Experiments," J. Am. Chem. Soc., 2002, vol. 124, pp. 7702-7709.
Fanali, G. et al.; "Human serum albumin: From bench to bedside," Mol. Asp. med., 2012, vol. 33, pp. 209-290.
Korzhnev, D. et al.; "Probing Invisible, Low-Populated States of Protein Molecules by Relaxation Dispersion NMR Spectroscopy: An Application to protein Folding." Acc. Chem. Res., 2008, vol. 41, pp. 442-451.
Krayukhina, E, et al.; "Aggregation analysis of pharmaceutical human immunoglobulin preparations using size-exclusion chromatography and analytical ultracentrifugation sedimentation velocity," J. Biosci. Bioeng. 2012, vol. 115, pp. 104-110.
Mao, X et al.; "Understanding Radiation Damping in a Simple Way," Concepts Magn. Reson. 1997, 9, 173.
Metz, H. et al.; "Benchtop-NMR and MRI—A new analytical tool in drug delivery research," Int. J. Pharm. 2008, 364, 170-175.
Oliva, A. et al.; "Influence of temperature and shaking on stability of insulin preparations: degradation kinetics," Int. J. Pharm., 1996, 143, 163-170.
Saso, L. et al.; "Effect of Selected Substances on Heat-Induced Aggregation of Albumin, IgG and Lysozyme," Res. Commun. Pathol. Pharmacol. 1998, 102, 15-28.
Baylor, N.W., Egan, W., Richman, P., (2002) Aluminum salts in vaccines—US perspective. Vaccine, 20, S18-S23.
Briggs, K.T., Taraban, M.B., Yu, Y.B. (2018) Water proton NMR detection of amide hydrolysis and diglycine dimerization. Chem. Comm. 54, 7003-7006.
Feng, Y., Taraban, M.B., Yu, Y.B. (2011) Linear dependency of NMR relaxation rates on shear modulus in hydrogels. Soft Matter, 7, 9890-9893.
Feng, Y., Taraban, M.B., Yu, Y.B., (2015) Water Proton NMR—A Sensitive Probe for Solute Association, Chem. Commun., 51, 6804-6807.
Guo, J., Lewis, L. M., Billones, H., Torres, E., Kolhe, P., (2016) The Effect of Shipping Stresses on Vaccine Re-dispersion Time. Journal of Pharmaceutical Sciences, 105, 2009-2013.
Kartoglu, U., Kenan Ozguler, N., Wolfson, L., Kurzatkowski, W., (2010) Validation of the shake test for detecting freeze damage to adsorbed vaccine. Bull. World Health Organ. 88, 624-631.
Khatun, R., Hunter, H.N., Sheng, Y., Carpick, BW., Kirkitadze, M.D., (2018) 27Al and 31P NMR spectroscopy method development to quantify aluminum phosphate in adjuvanted vaccine formulations. Journal of Pharmaceutical and Biomedical Analysis, 159, 166-172.
Neerasekare, G.M., Taraban, M.B., Shi, X., Jeong, E.-K., Trewhella, J., Yu, Y.B. (2011) Sol and gel states in peptide hydrogels visualized by Gd(III)-enhanced MRI Biopolymers (Pept. Sci.) 96, 734-743.
Levi, M. et al., (2017) The "Fluad Case" in Italy: Could it have been dealt differently? Human Vaccines & Immunotherapeutics, 13, 379-384.
Lewis, L. M., Guo, J., Torres, E., Wang, J., Billones, H., Kolhe, P., Young, A. L., Bates, D., Parker, A., Rigby-Singleton, S., (2017) Ex Situ and In Situ Characterization of Vaccine Suspensions in Pre-Filled Syringes. Journal of Pharmaceutical Sciences, 106, 2163-2167.
Lindblad, E.B., (2004) Aluminum compounds for use in vaccines. Immunology and Cell Biology, 82. 497-505, 82.
Mishra, A., Bhalla, S.R., Rawat, S., Bansal, V., Sehgal, R., Kumar, S., (2007) Standardization and validation of a new atomic absorption spectroscopy technique for determination and quantitation of Aluminium adjuvant in Immunobiologicals. Biologicals, 35, 277-284.
Muthurania, K., Ignatius, A. A.;, Jin, Z., Williams, J., Ohtake, S., (2015) Investigation of the sedimentation behavior of aluminum phosphate: influence of pH, ionic strength, and model Antigens. Journal of Pharmaceutical Sciences, 104, 3770-3781.
Petrovsky, N. (2015) Comparative safety of vaccine adjuvants: a summary of current evidence and future needs. Drug Safety, 38, 1059-1074.
Rohrer, M, Bauer, H., Mintorovitch, Jan., Requardt, M., Weinmann, H.J., (2005) Comparison of magnetic properties of MRI contrast media solutions at different magnetic field strengths. Invest. Radiol. 40, 715-724.
Signorelli, C., Odone, A., (2016) Dramatic 2015 excess mortality rate in Italy: a 9.1% increase that needs to be explained. Scand. J. Public Health, 44, 549-550.
Taraban, M.B., Truong, H.C., Feng, Y., Jouravleva, E.V., Anisimov, M.A., Yu, Y.B., (2015) Water Proton NMR for In Situ Detection of Insulin Aggregates, J. Pharm. Sci., 104, 4132-4141.
Taraban, M.B., Truong, H., Ilavsky, J., DePaz, R.A., Lobo, B., Yu, Y.B. (2017b) Non-invasive detection of nanoparticle clustering by water proton NMR. Transl. Mater. Res. 4, 025002.
Vecchi, S., Bufali, S., Skibinshi, D.A.G., O'hagan, D.T., Singh, M. (2011) Aluminum adjuvant dose guidelines in vaccine formulation for preclinical evaluations. J. Pharm. Sci. 101, 17-20.
Farrell, C, et al,; "Analytical Control Strategies for Aluminum," Vaccine Analytical Development, 2014, 1-29.
Taraban, Marc B., et al.; "Accessing Aluminum Vaccine Adjuvant Filling, Sedimentation, and Resuspension in Sealed Vials using Water Proton NMR," American Pharmaceutical Review, 2019, pp. 70-73.
Petrovsky, Nikolai; "Vaccine adjuvant safety: the elephant in the room," Expert Review of Vaccines, 2013, vol. 12, pp. 715-717.

(56) References Cited

OTHER PUBLICATIONS

Joint WHO-UNICEF Statement 2, Apr. 2010, "Who Recommends Recall and Destruction of All Lots of SHAN5 Vaccine as a Precautionary Measure," pp. 1-3.

* cited by examiner

IN SITU DETERMINATION OF ALUM FILLING EVENNESS AND SEDIMENTATION IN PHARMACEUTICAL PRODUCTS USING WATER PROTON NMR

CROSS REFERENCE TO RELATED APPLICATIONS

This application is filed under the provisions of 35 U.S.C. § 111(a) and claims priority to U.S. Provisional Patent Application No. 62/741,142 filed on Oct. 4, 2018 in the name of Yihua (Bruce) Y U et al. and entitled "In Situ Determination of Alum Filling Evenness and Sedimentation in Pharmaceutical Products using Water Proton NMR," which is hereby incorporated by reference herein in its entirety.

FIELD

The present invention relates to methods for noninvasive quality control of alum-containing products, including vaccines comprising alum adjuvants, using solvent nuclear magnetic resonance (NMR). The methods can be used to assess and the extent of alum particle sedimentation in sealed containers regardless of optical transparency of the alum-containing products.

DESCRIPTION OF THE RELATED ART

Adjuvants play a critical role in the efficacy of vaccines. The most widely used vaccine adjuvants are aluminum salt particles, more commonly referred to as alum. Presently, more than 20 vaccines contain alum adjuvants, including the anthrax, DTaP, DTaP/Hepatitis B/Polio, DTaP/Polio, DTaP/Polio/Hib, Hib, Hepatitis A, Hepatitis A/Hepatitis B, Hepatitis B, HPV, Meningococcus B, Pneumococcus, Tetanus and Diptheria Toxoids Adsorbed, TdaP, and the Diphtheria and Tetanus Toxoids Adsorbed vaccines.

The most commons alum salts include aluminum hydroxide, aluminum phosphate, and aluminum hydroxyphosphate sulfate [Baylor, 2002]. Alum particles are micron-sized with certain size heterogeneity [Lindblad, 2004]. Adjuvant dose in released products is related to vaccine safety and efficacy and adjuvant toxicity is of concern to vaccine safety [Petrovsky, 2015].

Disadvantageously, the alum particles are heavier than water and therefore tend to sediment and phase separate from water [Muthurania, 2015]. Sedimentation during manufacturing may cause the uneven filling of vials, resulting in vaccines with too much or too little alum adjuvant, which results in less than optimal immune responses in immunized subjects (too much may cause harm while too little may be ineffective). Filling levels of alum-adjuvanted vaccines are currently determined using atomic absorption microscopy [Mishra, 2007] or $^{27}Al/^{31}P$ NMR spectroscopy [Khatun, 2018].

Sedimentation during storage is unavoidable and requires shaking to fully resuspend the settled alum particles. Shipping stresses may make re-suspension difficult, with significant vial-to-vial variation [Guo, 2016]. Current qualitative in situ verification of vaccine re-suspension is the shake test [Kartoglu, 2010]. Current quantitative evaluation of vaccine re-suspension includes UV absorption spectroscopy (ex situ) [Guo, 2016], optical scanning analyzer (ex situ) [Muthurania, 2015] and microCT (in situ) [Lewis, 2017]. The ex situ techniques are destructive (as they require taking the drug substance out of its container) and perturbative (as they require dilution, pH adjustment, and other sample preparation steps). The in situ technique, micro-CT, involves ionizing radiation, which may damage the drug substance inside the container. All these techniques require ten minutes or longer for data acquisition as well as highly trained personnel for analysis.

The fundamental problem caused by destructive testing technologies for product quality control (QC) is that only a few units (i.e., vials, pre-filled syringes, etc.) are quantitatively inspected in each lot/batch. This leaves the possibility that defective products escape detection and thus are available to cause harm to patients. Because vaccines are typically administered to healthy people, a few adverse events in a large population cohort may cause panic in the public, leading to a decline in the vaccination rate [Signorelli, 2016; Levi, 2017].

There is a need for a fast and reliable technique which can be used for quality control in vaccine manufacturing, for example, the evenness of alum particle filling levels and/or the extent of alum particle sedimentation in sealed products in the distribution chain, from release to right before injection. Towards that end, the present invention relates to a method of using the transverse relaxation rate ($R_2$) of the solvent NMR signal, e.g., $R_2(^1H_2O)$, to determine the evenness of alum particle filling levels and/or the extent of alum particle sedimentation in filled and sealed products. Advantageously, the method described herein is easy to use, noninvasive, fast, and highly-sensitive.

SUMMARY

The present invention generally relates to a method of using NMR relaxation rates, specifically the transverse relaxation rate constant $R_2$ of solvent molecules, e.g., water, to determine the evenness of alum particle filling levels and/or the extent of alum particle sedimentation in alum-containing products such as filled and sealed vaccine products.

In one aspect, a method of determining the evenness of alum particle filling levels and/or the extent of alum particle sedimentation in an alum-containing product is described, said method comprising:
measuring the transverse relaxation rate of solvent $R_{2,m}$ in the alum-containing product; and
determining the evenness of alum particle filling levels and/or the extent of alum particle sedimentation in the alum-containing product by comparing the measured $R_{2,m}$ to a reference transverse relaxation rate of solvent $R_{2,r}$, wherein the reference $R_{2,r}$ represents an acceptable range of evenly distributed aluminum particles or suspected aluminum particles,
wherein when the measured $R_{2,m}$ is inside the reference $R_{2,r}$ range, the evenness of the alum particle filling levels and/or the alum particle resuspension is acceptable.

Other aspects, features and advantages of the invention will be more fully apparent from the ensuing disclosure and appended claims.

DETAILED DESCRIPTION, AND PREFERRED EMBODIMENTS THEREOF

The present invention generally relates to a method of using NMR relaxation rates, specifically the transverse relaxation rate constant $R_2$ of solvent molecules, e.g., water, to determine the evenness of alum particle filling levels and/or the extent of alum particle sedimentation in alum-containing products such as filled and sealed vaccine products.

Advantageously, the method described herein is a reliable and simple method to assess the extent of sedimentation in alum-containing products, e.g., vaccines comprising alum adjuvants, and hence has application as a quality control tool for any field utilizing alum-containing products, e.g., vaccine manufacturing. The method enables the non-destructive assessment of the alum-containing products, formulated as aqueous suspensions, without opening the vial or product container, by measuring the transverse nuclear spin relaxation rate constant, $R_2$, of a solvent, e.g., water. As will be discussed in detail hereinafter, uneven filling levels of alum particles or the sedimentation of same in the product containers are evidenced by a variation, either an increase or a decrease, of the transverse nuclear spin relaxation rate constant, $R_2$, of water. The $R_2$ constant of an alum-containing product, as well an acceptable range of $R_2$ constants of said alum-containing product (i.e., an acceptable range of evenly distributed aluminum particles or suspected aluminum particles), can be determined by the manufacturer. The acceptable range of $R_2$ constants can be provided on the package insert, on the vial label, or both. Thereafter, as new batches of alum-containing products are prepared, the $R_2$ constant of water of each new batch can be measured by the manufacturer to confirm the even filling of alum particles in the product containers before releasing same for sale and purchase. If the measured $R_2$ constant of the tested alum-containing product is outside of the reference range provided by the manufacturer, meaning that the vaccine dose is either too high or too low due to uneven alum particle filling, the specific vial containing the tested alum-containing product should be rejected. Further, the $R_2$ constant of water can be measured by the purchaser/user before use to confirm an acceptable resuspension of the alum particles in the alum-containing products pursuant to the manufacturer's guidelines. If the measured $R_2$ constant of the resuspended alum-containing product is outside of the reference range provided by the manufacturer, meaning that there was unacceptable resuspension, the tested alum-containing product should be rejected. Accordingly, this method redefines the conventional methods of evaluating the uneven filling and/or sedimentation of alum particles in aqueous suspensions comprising alum-containing products, e.g., vaccines, for each product container.

Reference herein to alum-containing products can include vaccines comprising alum adjuvants as well as pharmaceuticals comprising aluminum particles.

Recent breakthrough developments in the instrumentation for nuclear magnetic resonance (NMR) spectroscopy and imaging have opened up opportunities to design novel nondestructive analytical techniques for the nanoparticle industry. The analytical procedures become significantly faster with the application of commercially available computer-controlled NMR autosamplers. Of special importance was the appearance of commercially available, relatively inexpensive benchtop NMR and magnetic resonance imaging (MRI) instruments and relaxometers [Metz, 2008]. Benchtop NMR instruments enable highly accurate measurements of nuclear spin relaxation times $T_1$ and $T_2$. Moreover, most of these instruments have a permanent or electronically cooled magnet with the variable bore from 10 mm to 45 mm and even larger which provides a great flexibility in the nonintrusive measurements of vials of various sizes. Other known portable and handheld NMR instruments are known in the art and can be used to practice the methods described herein.

The present inventors have previously shown that the transverse relaxation rate of the water proton NMR signal, $R_2(^1H_2O)$, can be used to monitor solute association in aqueous solutions, such as gadolinium-chelate clustering inside hydrogels [Weerasekare, 2011], stiffness of hydrogels [Feng, 2011; U.S. Pat. No. 9,348,008], protein aggregation and surfactant micellization [Feng, 2015], insulin aggregation [Taraban, 2015], protein concentration [Yu, 2017], monoclonal antibody aggregation [Taraban, 2017a], nanoparticle clustering [Taraban, 2017b], and amide hydrolysis [Briggs, 2018]. Water proton NMR (wNMR) monitors water, which acts as a reporter for analytes dissolved in it. As a reporter, water has two tremendous advantages. First, its concentration far surpasses that of any analyte dissolved in it, by $10^3$-$10^6$ fold in most cases. This makes the $^1H_2O$ signal easily detectable by benchtop and other portable NMR instruments. Further, the solute association can be detected through the solvent NMR signal. Second, water is "endogenous" to all biomanufacturing processes and all biologic products, including vaccines. This sets it apart from "exogenous" reporters such as fluorescent dyes or radiotracers. The high concentration of "endogenous" water make it possible for wNMR to be contact-free in situ.

The essence of wNMR is a consistency check, which makes it useful for drug product manufacturing and inspection, where consistency is both critical and expected. For example, while wNMR cannot determine alum concentration directly, it can monitor consistency in alum filling and resuspension in vials. The same principle of consistency checking applies to monitoring emulsion droplet size, emulsion stability, antigen-alum complex stability, etc.

As defined herein, a "particle" corresponds to particles between about 1 nanometer and 50 microns in diameter, including particles that would be traditionally characterized as nanoparticles (e.g., about 1 nm to about 100 nm) and particles that would be traditionally characterized as micron-sized (e.g., up to about 10 microns). Particle size ranges relevant to the present invention include about 500 nm to about 1000 nm, about 1000 nm to about 5000 nm (5 microns), and about 1000 nm to about 10000 nm (10 microns). A person with an ordinary skill in the art will readily understand that the above particle size range is intended to be unlimited and could be extended to smaller and/or larger sizes. Also, it should be appreciated that the particles can be any shape, including spherical, can be substantially symmetrical or asymmetrical, and/or can be a single particle or be present as an aggregate of particles having an average aggregate size in a range from about 100 nm to about 10 microns or about 500 nm to about 1000 nm, about 1000 nm to about 5000 nm (5 microns), or about 1000 nm to about 10000 nm (10 microns). It should be understood by the person skilled in the art that the "particles" can be free aluminum particles or aluminum-antigen complexes, or a mixture of free aluminum particles and aluminum-antigen complexes.

As defined herein, the "alum-containing product" includes a product with nano- and micron-sized particles comprising aluminum and suspended in a solvent or a mixture of solvents. The alum-containing product can further comprise at least one surfactant, at least one water-soluble organic solvent, at least one dispersant, at least one biocide, at least one buffering agent, at least one pH adjusting agent (e.g., acids and/or bases), with or without antigens, or any combination thereof, as readily determined by the person skilled in the art. Many vaccines are alum-containing products because of the presence of an aluminum adjuvant.

As defined herein, a "vial" corresponds to a container, vessel, bottle, syringe, injection pen, or ampoule used to store the vaccine or other alum-containing product, wherein the vial comprises glass, plastic, ceramic, rubber, elastomeric material, and/or anything non-magnetic metal. The vial can have a screw top, a top that is closed using a cork or plastic stopper, a crimp vial (closed with a rubber stopper and a metal cap), a flip-top, a snap cap, or any other article of manufacture used to seal or close a vial. The vial can be tubular or cylindrical, or have a bottle-like shape with a neck. Other types and shapes of vials used to store particles as well as caps are readily understood by the person skilled in the art. The vials can be optically transparent or not optically transparent. There is no need to peel off any label on the vial, regardless of whether the label is transparent or not.

It is understood by the person skilled in the art that the "measuring" of the transverse relaxation rate of solvent $R_2$ is may be done by measuring some other parameter and converting to the $R_2$ value.

As defined herein, a "non-destructive" measurement is defined as a measurement performed without opening the vial or otherwise accessing the contents of the vial (for example by withdrawing a portion through a rubber gasket). Moreover, a non-destructive measurement means that no additives or probes or the like are added to the vial prior to the measurement of the transverse relaxation rate of solvent $R_2$ in the alum-containing product. Non-destructive also means that there is no need to make the vials optically transparent and no need to peel off any labels on the vials.

As defined herein, "alum" corresponds to aluminum-containing salts comprising one or more of aluminum hydroxide, aluminum phosphate, alum $(KAl(SO_4).12H_2O)$, aluminum hydroxyphosphate sulfate, as well as other known or proprietary aluminum salts that can be used as alum adjuvants or in pharmaceutical products comprising aluminum.

As defined herein, "DS" is a drug substance, which refers to the bulk drug solution or suspension or emulsion.

As defined herein, "DP" is a drug product, which is the combination of the DS plus the container or vial. In other words, DP refers to filled (partially or fully), sealed and labeled vials comprising the DS.

Suspensions and emulsions have complex hydrodynamic behavior, which might complicate the very last step of product manufacturing, the fill-finish step. For example, alum particles tend to sediment in water, which may lead to uneven filling of vials from the batch. As defined herein, the "evenness of alum particle filling levels" corresponds to a consistent alum particle concentration in each of the vials filled. For example, if the concentration of alum particles in the vial is expected to be a mean value of x mg/mL, then the evenness of alum particle filling levels corresponds to the assessment that the vial contains a mean value of x mg/mL±5% of the mean, which is typical of accepted United States Pharmacopeia (USP) variability If the alum particle concentration isn't consistent in all of the vials filled, pursuant to the specification of the alum-containing product, then product with too much or too little alum will be administered to the patient, with possible deleterious effects. More precisely, too much alum may cause harm while too little may render the alum-containing product, e.g., the vaccine, ineffective. Accordingly, if the alum particle concentration isn't consistent, i.e., the alum particle filling levels are not even, then the vial should not pass the quality control specifications. Notably, the method of using the transverse nuclear spin relaxation rate constant, $R_2$, of water, as described herein, cannot determine alum concentration directly, but instead monitors the consistency in the alum concentration from one vial to another.

The "extent of alum particle sedimentation" is a measure of whether the alum-containing product in the vial is properly resuspended following settling and/or transport and/or storage. Transport and storage may involve exposure of the alum-containing product to a variety of stressors including, but not limited to, temperature fluctuations, pH changes, vigorous shaking during transportation, exposure to sunlight, and freezing. The method of using the transverse nuclear spin relaxation rate constant, $R_2$, of water, as described herein, cannot quantitate the sedimentation directly, but instead monitors the consistency in the sedimentation over time and subsequent to possible stressors.

The present inventors have surprisingly discovered that solvent NMR can be used to monitor and detect the evenness of alum particle filling levels and/or the extent of alum particle sedimentation in alum-containing products, e.g., vaccine products, in filled and sealed vials. Both the manufacturer as well as commercial end users and researchers can use solvent NMR to noninvasively inspect alum-containing products. In addition to being noninvasive, additional advantages of low field solvent NMR includes low cost instrumentation (e.g., a desktop NMR), simple and rapid data acquisition and analysis, minimal technical expertise, and results that are readily available within<5 min. It should be appreciated that the measurements can occur destructively as well, whereby the vial is opened, as readily determined by the person skilled in the art. Further, the method described herein can utilize high field NMR, if needed.

The method described herein is fast and reliable and allows the user to determine the evenness of alum particle filling levels and/or the extent of alum particle sedimentation in alum-containing products, e.g., vaccines, as described herein.

In practice, the standard for evenness of alum particle filling levels and/or extent of alum particle sedimentation in the alum-containing product should be determined by the manufacturer. The manufacturer can provide the acceptable $R_2(^1H_2O)$ range in $sec^{-1}$, i.e., a reference range, for the alum-containing product at a given temperature (e.g., 25° C.) and magnetic field strength (e.g., 0.5 T). The user will then measure the $R_2(^1H_2O)$ of the alum-containing product at the same temperature and magnetic field strength and compare the measured $R_2(^1H_2O)$ value with the manufacturer-specified acceptable range of $R_2(^1H_2O)$, i.e., reference, as understood by the person skilled in the art, to determine if the alum particle filling levels were even (during the fill-finish step) and/or the alum-containing product has been resuspended properly (following storage and/or transport).

Accordingly, in a first aspect, a method of determining the evenness of alum particle filling levels and/or the extent of alum particle sedimentation in an alum-containing product is described, said method comprising: measuring the transverse relaxation rate of solvent $R_{2,m}$ in the alum-containing product; and determining the evenness of alum particle filling levels and/or the extent of alum particle sedimentation in the alum-containing product by comparing the measured $R_{2,m}$ to a reference transverse relaxation rate of solvent $R_{2,r}$, wherein the reference $R_{2,r}$ represents an acceptable range of evenly distributed aluminum particles or suspected aluminum particles, wherein when the measured $R_{2,m}$ is inside the reference $R_{2,r}$ range, the alum particle filling levels and/or the alum particle resuspension is acceptable. In one embodiment, the alum-containing product is a vaccine that comprises an alum-containing adjuvant. The transverse relaxation rate of solvent $R_2$ can be determined using solvent NMR, preferably low field solvent NMR. The measuring of the transverse relaxation rate of solvent $R_2$ in the alum-containing product can be done non-invasively in a vial. The reference $R_{2,r}$ range, at a specified temperature, can be measured by the manufacturer and the result listed in the package insert and/or the vial of the alum-containing product. Preferably $R_{2,m}$ is measured at substantially the same temperature as $R_{2,r}$. The distributor or purchaser can then use NMR, e.g., benchtop, portable, or handheld, to measure $R_{2,m}$ at the specified temperature and compare it with the reference $R_{2,r}$ range listed in the package insert or vial before distribution or usage. If the evenness of alum particle filling levels and/or the extent of alum particle suspension is outside of the acceptable range determined by the manufacturer, and as such is unintended, that specific vial of alum-containing product should not be distributed or used immediately. It should be appreciated that if the evenness of alum particle filling levels and/or the extent of alum particle suspension is outside of the acceptable range determined by the manufacturer, the vial(s) can be shaken for additional time and the $R_{2,m}$ remeasured to verify that the alum-containing product should be removed from distribution or use.

It should be appreciated that the transverse relaxation time $T_2$, which is the inverse of the transverse relaxation rate $R_2$, can be reported as the reference instead and the user uses the transverse relaxation time of solvent $T_2$ of the alum-containing product to determine the evenness of alum particle filling levels and/or the extent of alum particle sedimentation, as readily understood by the person skilled in the art. For example, in one embodiment of the first aspect, a method of determining the evenness of alum particle filling levels and/or the extent of alum particle sedimentation in an alum-containing product using the transverse relaxation time $T_2$, of a solvent is described, said method comprising measuring the transverse relaxation time of solvent $T_{2,m}$ in the alum-containing product, and determining the evenness of alum particle filling levels and/or the extent of alum particle sedimentation in the alum-containing product by comparing the measured $T_{2,m}$ to a reference transverse relaxation time of solvent $T_{2,r}$, wherein the reference $T_{2,r}$ represents an acceptable range of evenly distributed aluminum particles or suspected aluminum particles, wherein when the measured $T_{2,m}$ is inside the reference $T_{2,r}$ range, the evenness of the alum particle filling levels and/or the alum particle resuspension is acceptable. The alum-containing product can be a vaccine that comprises an alum-containing adjuvant. The transverse relaxation time of solvent $T_2$ can be determined using solvent NMR, preferably low field solvent NMR. The measuring of the transverse relaxation time of solvent $T_2$ in the alum-containing product can be done non-invasively in a vial. The reference $T_{2,r}$ range, at a specified temperature, can be measured by the manufacturer and the result listed in the package insert and/or the vial of the alum-containing product. Preferably $T_{2,m}$ is measured at substantially the same temperature as $T_{2,r}$. The distributor or purchaser can then use NMR, e.g., benchtop, portable, or handheld, to measure $T_{2,m}$ at the specified temperature and compare it with the reference $T_{2,r}$ range listed in the package insert or vial before distribution or usage. If the evenness of alum particle filling levels and/or the extent of alum particle suspension is outside of the acceptable range determined by the manufacturer, and as such is unintended, that specific vial of alum-containing product should not be distributed or used immediately. It should be appreciated that if the evenness of alum particle filling levels and/or the extent of alum particle suspension is outside of the acceptable range determined by the manufacturer, the vial(s) can be shaken for additional time and the $T_{2,m}$ remeasured to verify that the alum-containing product should be removed from distribution or use.

Although not wishing to be bound by this method, in one embodiment, i. the evenness is determined by verifying the alum level in the DS batch using destructive methods known in the art. Then the vials can be filled to obtain a DP. ii. Thereafter, the manufacturer can measure the $R_2(^1H_2O)$ of some or all vials in the batch to determine if the vials have the same level of filling, e.g., are even or consistent. iii. Then, the DP level of a few vials in the batch can be verified using destructive methods to demonstrate that not only do all vials have the same filling level, but also the correct filling level. It should be appreciated that the order of steps ii and iii can be switched.

An example of the advantages associated with the methods described herein are as follows. The maximum allowed aluminum dose is 0.85 mg $Al^{3+}$, according to the US Code of Federal Regulations [Vecchi, 2011]. The highest concentration of $Al^{3+}$ in FDA-approved vaccines on the market is 1.2 mg/mL in BIOTHRAX. BIOTHRAX is packaged as 5-mL multi dose vials, wherein each dose is 0.6 mg/mL, below the federal limit of 0.85 mg/mL. The alum adjuvant in BIOTHRAX is aluminum hydroxide. If the vials are filled unevenly, and the deviation is +42%, then 0.5 mL will contain 0.852 mg or more $Al^{+3}$, which exceeds the federal limit. Advantageously, a 42% (or more) deviation is easily detected using the methods described herein. Further, if the multi-dose vial is resuspended improperly, then some doses may contain $Al^{+3}$ higher than 0.6 mg and some doses may contain less, with the exact amounts unknown. Advantageously, the methods described herein can be used to detect alum resuspension levels before and after each dose is drawn from the vial, which allows the user to more accurately know the dose for each draw.

The present inventors have thus disclosed a nondestructive quality control technology using solvent NMR to determine the evenness of alum particle filling levels and/or the extent of alum particle sedimentation in alum-containing products, e.g., vaccines. This allows for the manufacturer and/or distributor, and/or end user to monitor for unexpected anomalies, e.g., too much or too little alum adjuvant, batch-to-batch variations of the same product, and/or if the alum-containing product was properly resuspended following transport and/or storage stressors. This can be done without opening the vial or peeling off the label. Further advantages include the applicability of the method for both continuous and batch unit manufacturing operations, both anti-bacterial and anti-viral vaccines, and/or both drug products and drug substances.

It should be appreciated that the methods defined herein are identifying a characteristic of the solutions that is different than the level of clustering or the extent of aggregation previously disclosed by the present inventors. "Aggregation" of biopharmaceuticals is understood to be driven by hydrophobic and/or hydrophilic interactions of proteins while "clustering" of particles is understood to be a phase separation of the particles from the solvent as a result of particle assembly which, unlike aggregation, is not driven by hydrophobic and/or hydrophilic interactions. In clustering, solvent molecules are trapped in the restricted compartments inside the clusters of particles. The currently described method involves sedimentation, which relates to the settling of more dense particles in a solvent, wherein if the particles are not evenly distributed in the solution, there is an uneven dose of the alum-containing product per unit volume. There is no known aggregation or clustering that impacts the evenness of filling or the resuspension of particles in the alum-containing product.

The features and advantages of the invention are more fully shown by the illustrative examples discussed below.

EXAMPLE 1

The transverse relaxation rate of the water proton NMR signal, $R_2(^1H_2O)$, response to the filling level of alum in sealed vials has been studied. Different concentrations of alum in water were used to simulate the variations of the alum filling levels under manufacturing conditions.

Five aqueous suspensions of alum in water with various alum concentrations were prepared at the Infectious Disease Research Institute (IDRI). The concentrations of alum in water were 0.1 mg/mL, 0.5 mg/mL, 1.0 mg/mL, 2.0 mg/mL, and 5.0 mg/mL. Four mL of each alum suspension was introduced inside in a glass vial (4 mL max volume), sealed with rubber stopper, and secured by a metal cap.

The $R_2(^1H_2O)$ in $sec^{-1}$ of each alum suspension was measured at 0.56 T (23.8 MHz $^1H$ resonance frequency) at 22° C. To measure the transverse relaxation rate constant $R_2$, Carr-Purcell-Meiboom-Gill (CPMG) experiments were used. It should be appreciated by the person skilled in the art that there are other methods to determine $R_2$ and the use of CPMG in the examples described herein are not intended to limit the determination of $R_2$. The transverse relaxation time $T_2$ ($=1/R_2$) value can be extracted by fitting experimental data to Formula (1):

$$I(t)=I_0\times\exp(-t/T_2) \qquad (1)$$

where I(t) is the $^1H_2O$ signal intensity at time t, $I_0$ is the initial $^1H_2O$ signal intensity when t=0, and t is the $T_2$ delay time.

Measurements of $R_2(^1H_2O)$ in $sec^{-1}$ were performed noninvasively, without opening the vial, since the wide bore (26 mm ID) of the probe of the low-field NMR spectrometer (0.56 T) permitted the accommodation of the vial without drawing a portion of the sample and transferring it into standard NMR tube.

Figures 1, 2A, 2B:
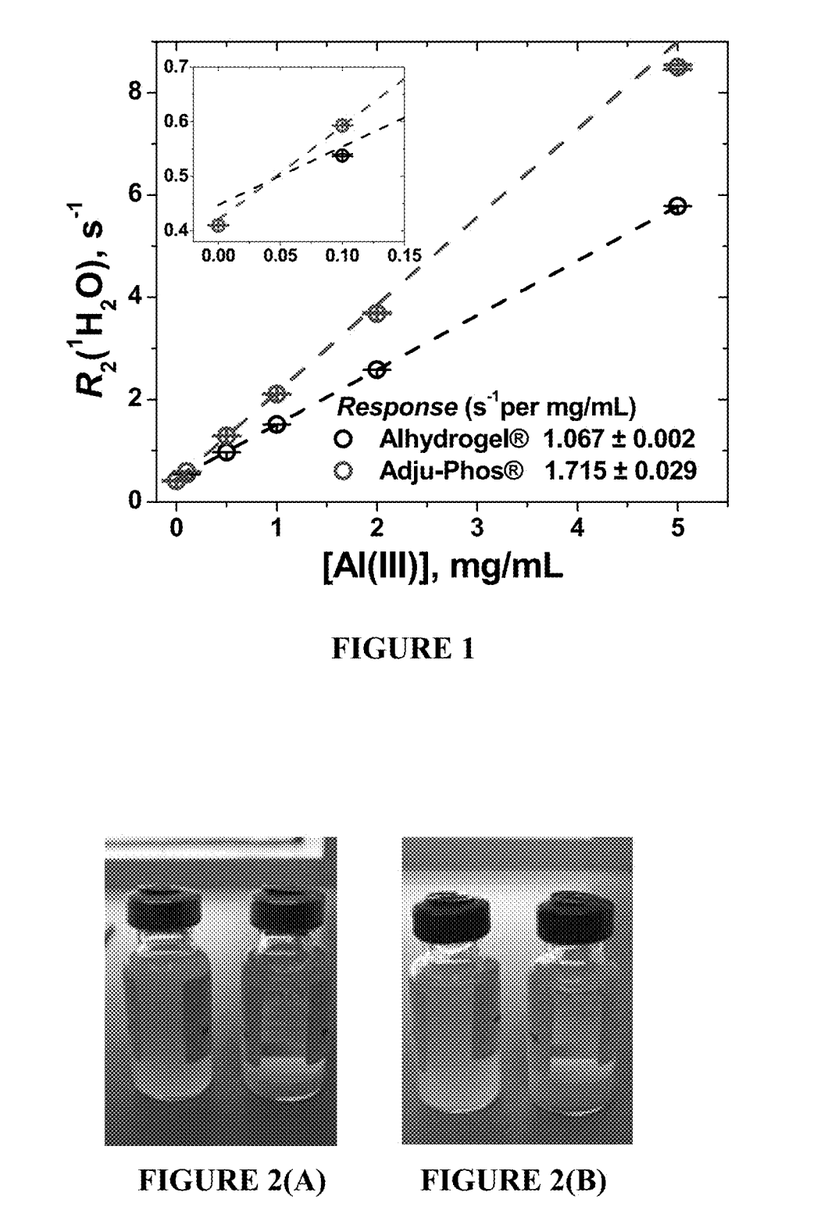
FIG. 1. Dependence of water proton transverse relaxation rate $R_2(^1H_2O)$ on alum concentration (full suspension) for two alum adjuvants. The insert shows the region of typical alum salt concentration in many vaccine products.
FIG. 2(A). Fully suspended (left) and sedimented (after one week of sedimentation) aqueous suspension of Alhydrogel® in a sealed vial.
FIG. 2(B). Fully suspended (left) and sedimented (after one week of sedimentation) aqueous suspension of Adju-Phos® in a sealed vial.

The values of the transverse relaxation rate of water $R_2(^1H_2O)$ measured in alum suspensions with different concentrations of alum are shown in FIG. 1. FIG. 1 presents the results at 0.56 T from the CPMG pulse sequence at interpulse delay τ=300 μsec, where error bars represent the standard deviation of three consecutive measurements.

As seen from FIG. 1, the values of the transverse relaxation rate of water $R_2(^1H_2O)$ demonstrate strong sensitivity towards the changes in alum concentration in aqueous solutions. The slope the linear fit of the $R_2(^1H_2O)$ vs. the alum concentration response, called relaxivity, is 1.07 (mg/mL)$^{-1}\cdot s^{-1}$ for Alhydrogel® and 1.71 (mg/mL)$^{-1}\cdot s^{-1}$ for Adju-Phos® at 0.56 T. To put matter in perspective, the relaxivity of nine FDA approved gadolinium-based contrast agents (GBCAs) is in the range of 4.26-8.54 (mg/mL)$^{-1}\cdot s^{-1}$ at 0.47 T [Rohrer, 2005]. Considering alum salts are diamagnetic while GBCAs are paramagnetic, the particulate nature (micron-sized) of alum salts render them very efficient in causing water proton transverse relaxation.

Typically, the alum level in vaccine products is 0.5-1.0 mg/mL. A 5% filling deviation from 0.5 mg/mL is 0.025 mg/mL, which leads to a change of $R_2(^1H_2O)$ of 0.027 $s^{-1}$. The error in $R_2(^1H_2O)$ measurements is ~0.0005 $s^{-1}$. This makes it possible to detect even <5% deviations in alum filling levels for the alum concentrations used in vaccine manufacturing.

EXAMPLE 2

The transverse relaxation rate of the water proton NMR signal, $R_2(^1H_2O)$, response to the sedimentation of the alum in sealed vials has been studied. Alum samples prepared and studied in the Example 1 with different concentrations of alum in water were used to study the sedimentation effects.

Five alum samples from Example 1 were kept undisturbed for 1 week at 4° C. to allow complete settling of the alum particles. After equilibration to 22° C., the sealed glass vials containing settled alum particles were carefully transferred into the probe of the NMR instrument for $R_2(^1H_2O)$ detection. FIG. 2(A) and 2(B) shows photos of a vial containing fully suspended alum particles and another vial containing fully settled alum particles, respectively.

The $R_2(^1H_2O)$ of each alum suspension was measured at 0.56 T (23.8 MHz 1H resonance frequency) using Carr-Purcell-Meiboom-Gill (CPMG) pulse sequence. Data collection and processing were the same as described in the Example 1. Similar to the Example 1, the measurements of $R_2(^1H_2O)$ were performed noninvasively, without opening the vial. It should be appreciated by the person skilled in the art that there are other methods to determine $R_2$ and the use of CPMG in the examples described herein are not intended to limit the determination of $R_2$.

Figure 3A:
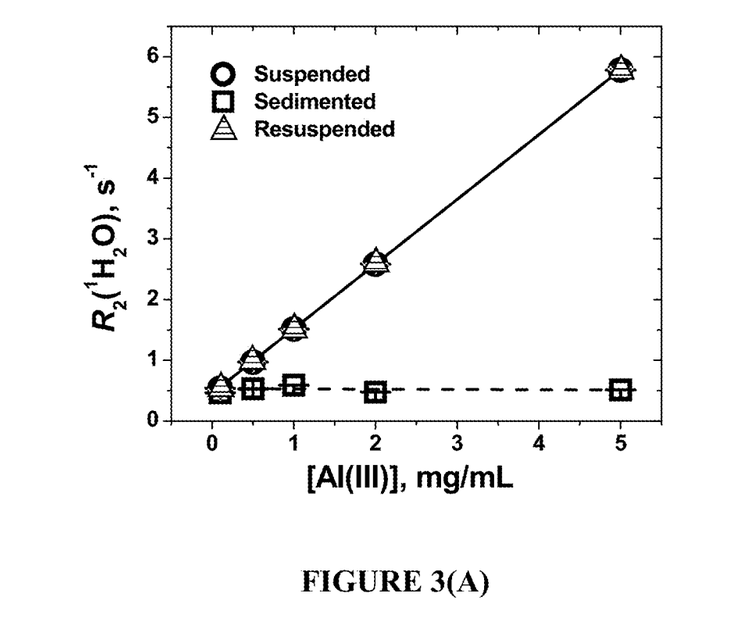
FIG. 3(A). $R_2(^1H_2O)$ vs. aluminum salt concentration observed for suspended, sedimented and resuspended Alhydrogel®. In each panel, solid and dashed lines represent suspended and sedimented aluminum salt, respectively.
Figure 3B:
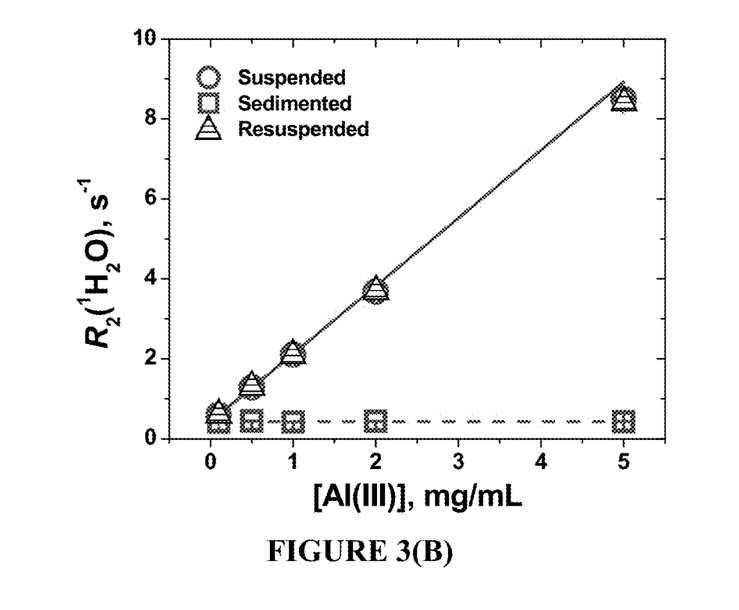
FIG. 3(B). $R_2(^1H_2O)$ vs. aluminum salt concentration observed for suspended, sedimented and resuspended Adju-Phos®. In each panel, solid and dashed lines represent suspended and sedimented aluminum salt, respectively.

The values of the transverse relaxation rate of water $R_2(^1H_2O)$ measured in the settled alum particles with different concentrations of alum are shown in FIG. 3. FIG. 3 compares the results of the $R_2(^1H_2O)$ concentration dependence (circles) of fully suspended alum samples (i.e., Example 1) with the values $R_2(^1H_2O)$ observed in fully sedimented alum samples (squares) at different concentrations. The error bars in FIG. 3 represent the standard deviation of three consecutive measurements and varies within 0.005-0.001 $s^{-1}$.

As seen from FIG. 3, the values of the transverse relaxation rate of water $R_2(^1H_2O)$ for settled alum particles are strikingly different from their fully suspended counterparts. This makes $R_2(^1H_2O)$ a reliable and sensitive probe of the suspension uniformity in vaccine formulations.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

Baylor, N. W., Egan, W., Richman, P., (2002) Aluminum salts in vaccines—US perspective. *Vaccine*, 20, S18-S23.

Briggs, K. T., Taraban, M. B., Yu, Y. B. (2018) Water proton NMR detection of amide hydrolysis and diglycine dimerization. Chem. Comm. 54, 7003-7006.

Feng, Y., Taraban, M. B., Yu, Y. B. (2011) Linear dependency of NMR relaxation rates on shear modulus in hydrogels. Soft Matter, 7, 9890-9893.

Feng, Y., Taraban, M. B., Yu, Y. B., (2015) Water Proton NMR—A Sensitive Probe for Solute Association, *Chem. Commun.*, 51, 6804-6807.

Guo, J., Lewis, L. M., Billones, H., Torres, E., Kolhe, P., (2016) The Effect of Shipping Stresses on Vaccine Redispersion Time. *Journal of Pharmaceutical Sciences*, 105, 2009-2013.

Kartoglu, U., Kenan Ozguler, N., Wolfson, L., Kurzatkowski, W., (2010) Validation of the shake test for detecting freeze damage to adsorbed vaccine. *Bull. World Health Organ.* 88, 624-631.

Khatun, R., Hunter, H. N., Sheng, Y., Carpick, B W., Kirkitadze, M. D., (2018) $^{27}$Al and $^{31}$P NMR spectroscopy method development to quantify aluminum phosphate in adjuvanted vaccine formulations. *Journal of Pharmaceutical and Biomedical Analysis*, 159, 166-172.

Levi, M. et al., (2017) The "Fluad Case" in Italy: Could it have been dealt differently? *Human Vaccines & Immunotherapeutics*, 13, 379-384

Lewis, L. M., Guo, J., Tones, E., Wang, J., Billones, H., Kolhe, P., Young, A. L., Bates, D., Parker, A., Rigby-Singleton, S., (2017) Ex Situ and In Situ Characterization of Vaccine Suspensions in Pre-Filled Syringes. *Journal of Pharmaceutical Sciences*, 106, 2163-2167.

Lindblad, E. B., (2004) Aluminum compounds for use in vaccines. *Immunology and Cell Biology*, 82. 497-505, 82.

Metz, H., Mäder, K., (2008) Benchtop-NMR and MRI—a new analytical tool in drug delivery research, *Int. J. Pharm.*, 364, 170-178.

Mishra, A., Bhalla, S. R., Rawat, S., Bansal, V., Sehgal, R., Kumar, S., (2007) Standardization and validation of a new atomic absorption spectroscopy technique for determination and quantitation of Aluminium adjuvant in immunobiologicals. *Biologicals*, 35, 277-284.

Muthurania, K., Ignatius, A. A., Jin, Z., Williams, J., Ohtake, S., (2015) Investigation of the sedimentation behavior of aluminum phosphate: influence of pH, ionic strength, and model Antigens. *Journal of Pharmaceutical Sciences*, 104, 3770-3781.

Petrovsky, N. (2015) Comparative safety of vaccine adjuvants: a summary of current evidence and future needs. Drug Safety, 38, 1059-1074.

Rohrer, M, Bauer, H., Mintorovitch, Jan., Requardt, M., Weinmann, H. J., (2005) Comparison of magnetic properties of MRI contrast media solutions at different magnetic field strengths. Invest. Radiol. 40, 715-724.

Signorelli, C., Odone, A., (2016) Dramatic 2015 excess mortality rate in Italy: a 9.1% increase that needs to be explained. *Scand. J. Public Health*, 44, 549-550.

Taraban, M. B., Truong, H. C., Feng, Y., Jouravleva, E. V., Anisimov, M. A., Yu, Y. B., (2015) Water Proton NMR for In Situ Detection of Insulin Aggregates, *J. Pharm. Sci.*, 104, 4132-4141.

Taraban, M. B., DePaz, R. A., Lobo, B., Yu, Y. B. (2017a) Water proton NMR: a tool for protein aggregation characterization. Anal. Chem. 89, 5494-5502.

Taraban, M. B., Truong, H., Ilaysky, J., DePaz, R. A., Lobo, B., Yu, Y. B. (2017b) Non-invasive detection of nanoparticle clustering by water proton NMR. Transl. Mater. Res. 4, 025002.

Vecchi, S., Bufali, S., Skibinshi, D. A. G., O'hagan, D. T., Singh, M. (2011) Aluminum adjuvant dose guidelines in vaccine formulation for preclinical evaluations. J. Pharm. Sci. 101, 17-20.

Weerasekare, G. M., Taraban, M. B., Shi, X., Jeong, E.-K., Trewhella, J., Yu, Y. B. (2011) Sol and gel states in peptide hydrogels visualized by Gd(III)-enhanced MRI. Biopolymers (Pept. Sci.) 96, 734-743.

Yu, Y. B., Feng, Y., Taraban, M. B. (2017) Water proton NMR for noninvasive chemical analysis and drug product inspection. Am. Pharmaceut. Rev. 20, 34-39.

What is claimed is:

1. A method of determining alum particle filling level evenness and/or an extent of alum particle sedimentation in an alum-containing product, said method comprising:
measuring a transverse relaxation rate of solvent $R_{2,m}$ in the alum-containing product; and
determining the alum particle filling level evenness and/or the extent of alum particle sedimentation in the alum-containing product by comparing the measured $R_{2,m}$ to a reference transverse relaxation rate of solvent $R_{2,r}$, wherein the reference $R_{2,r}$ represents an acceptable range of evenly distributed aluminum particles or suspended aluminum particles,
wherein when the measured $R_{2,m}$ is inside the reference $R_{2,r}$ range, the evenness of the alum particle filling levels and/or the extent of alum particle sedimentation is acceptable.

2. The method of claim 1, wherein $R_{2,m}$ is measured using nuclear magnetic resonance (NMR).

3. The method of claim 1, wherein the alum-containing product is contained in a vial, and wherein no additives or probes are added to the vial prior to measurement of the transverse relaxation rate of solvent $R_{2,m}$.

4. The method of claim 3, wherein $R_{2,m}$ is measured without opening the vial or withdrawing the contents of the vial containing the alum-containing product.

5. The method of claim 1, wherein the solvent is water.

6. The method of claim 1, wherein the alum-containing product comprises particles in a range from 1 nanometer and 50 microns in diameter.

7. The method of claim 1, wherein the alum-containing product comprises aluminum-containing salts selected from the group consisting of aluminum hydroxide, aluminum phosphate, alum (KAl(SO$_4$).12H$_2$O), aluminum hydroxyphosphate sulfate, and any combination thereof.

8. The method of claim 1, wherein the alum-containing product is a vaccine comprising alum adjuvants or a pharmaceutical product comprising aluminum particles.

9. The method of claim 1, wherein acceptable alum particle filling levels and/or acceptable alum particle sedimentation indicates that the alum-containing product is useable or distributable as intended.

10. The method of claim 1, wherein the alum-containing product comprises particles in a range from 1000 nm to 10000 nm.

11. The method of claim 1, wherein $R_{2,m}$ and $R_{2,r}$ are measured at a substantially similar temperature.

12. A method of determining alum particle filling level evenness and/or an extent of alum particle sedimentation in an alum-containing product, said method comprising:
   measuring a transverse relaxation time of solvent $T_{2,m}$ in the alum-containing product; and
   determining alum particle filling level evenness and/or the extent of alum particle sedimentation in the alum-containing product by comparing the measured $T_{2,m}$ to a reference transverse relaxation time of solvent $T_{2,r}$, wherein the reference $T_{2,r}$ represents an acceptable range of evenly distributed aluminum particles or suspended aluminum particles,
   wherein when the measured $T_{2,m}$ is inside the reference $T_{2,r}$ range, the evenness of the alum particle filling levels and/or the extent of alum particle sedimentation is acceptable.

13. The method of claim 12, wherein $T_{2,m}$ is measured using nuclear magnetic resonance (NMR).

14. The method of claim 13, wherein the NMR is portable.

15. The method of claim 12, wherein the alum-containing product is contained in a vial, and wherein no additives or probes are added to the vial prior to measurement of the transverse relaxation time of solvent $T_{2,m}$.

16. The method of claim 15, wherein $T_{2,m}$ is measured without opening the vial or withdrawing the contents of the vial containing the alum-containing product.

17. The method of claim 12, wherein the solvent is water.

18. The method of claim 12, wherein the alum-containing product comprises aluminum-containing salts selected from the group consisting of aluminum hydroxide, aluminum phosphate, alum ($KAl(SO_4).12H_2O$), aluminum hydroxyphosphate sulfate, and any combination thereof.

19. The method of claim 12, wherein the alum-containing product is a vaccine comprising alum adjuvants or a pharmaceutical product comprising aluminum particles.

20. The method of claim 12, wherein acceptable alum particle filling levels and/or acceptable alum particle sedimentation indicates that the alum-containing product is useable or distributable as intended.

* * * * *